(12) United States Patent
Wang

(10) Patent No.: US 9,034,163 B1
(45) Date of Patent: May 19, 2015

(54) ELECTRODE FOR CAPILLARY ELECTROPHORESIS

(71) Applicant: Tiansong Wang, Shoreline, WA (US)

(72) Inventor: Tiansong Wang, Shoreline, WA (US)

( * ) Notice: Subject to any disclaimer, the term of this patent is extended or adjusted under 35 U.S.C. 154(b) by 421 days.

(21) Appl. No.: 13/682,533

(22) Filed: Nov. 20, 2012

(51) Int. Cl.
*G01N 27/403* (2006.01)
*G01N 27/447* (2006.01)

(52) U.S. Cl.
CPC .... *G01N 27/44708* (2013.01); *G01N 27/44756* (2013.01); *G01N 27/447* (2013.01)

(58) Field of Classification Search
CPC .................................. G01N 27/447–27/44795
See application file for complete search history.

(56) References Cited

U.S. PATENT DOCUMENTS 5,364,521 A * 11/1994 Zimmermann ............... 204/604

* cited by examiner

*Primary Examiner* — J. Christopher Ball
(74) *Attorney, Agent, or Firm* — David Pressman

(57) ABSTRACT

An electrode assembly for capillary electrophoresis (CE) comprises a manifold (310), a connector (305) a sheath (300), and a seal (325). A capillary tube (100) passes through the manifold, the connector, the sheath, and the seal, stopping just beyond the end of the sheath. The sheath is fillable with water (330) or another fluid that cools the capillary tube in the vicinity of the electrode, thereby preventing degradation of a sample due to heat. The sheath may be metal or plastic with a metal sleeve electrode on its exterior. The sheath is sufficiently strong to penetrate a rubber or other pierceable cap on a vial. The manifold and connector incorporate an air path (605, 312, 307) so that when the electrode is fully inserted into a vial, the contents (650) of the vial are at atmospheric pressure (or another applied pressure or vacuum).

17 Claims, 4 Drawing Sheets

Figure 12:
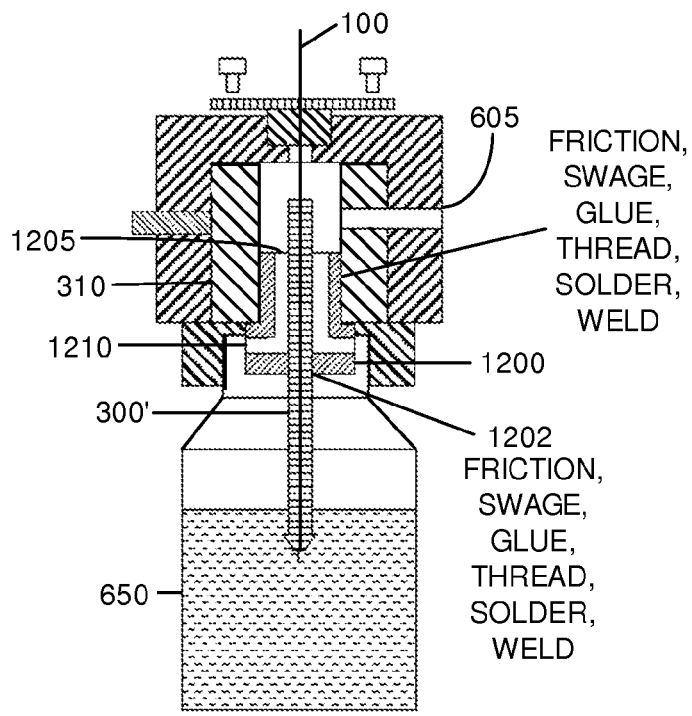

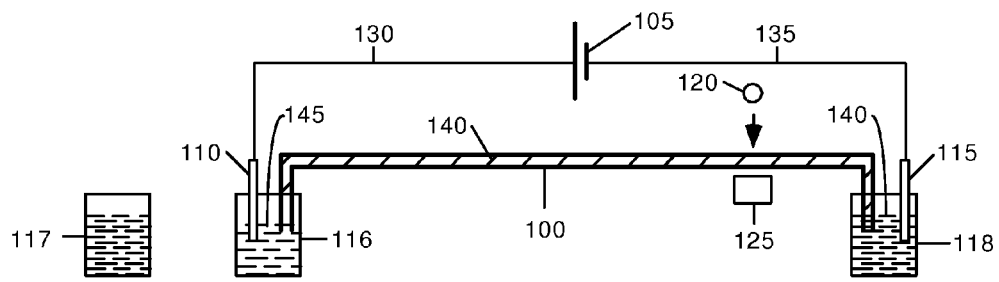
Fig. 1--Prior Art--Load Sample
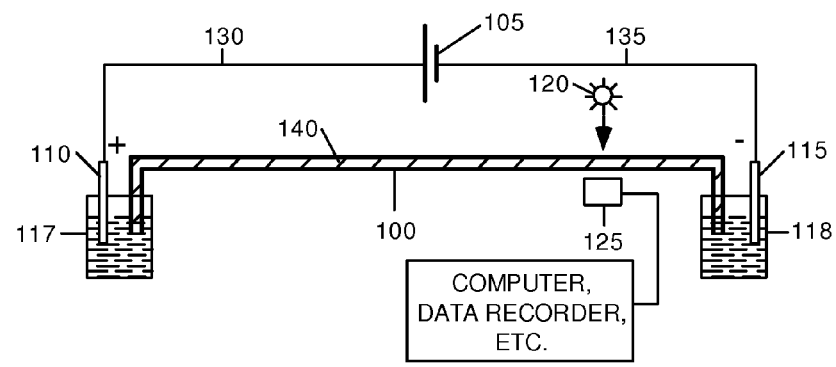
Fig. 2--Prior Art--Run
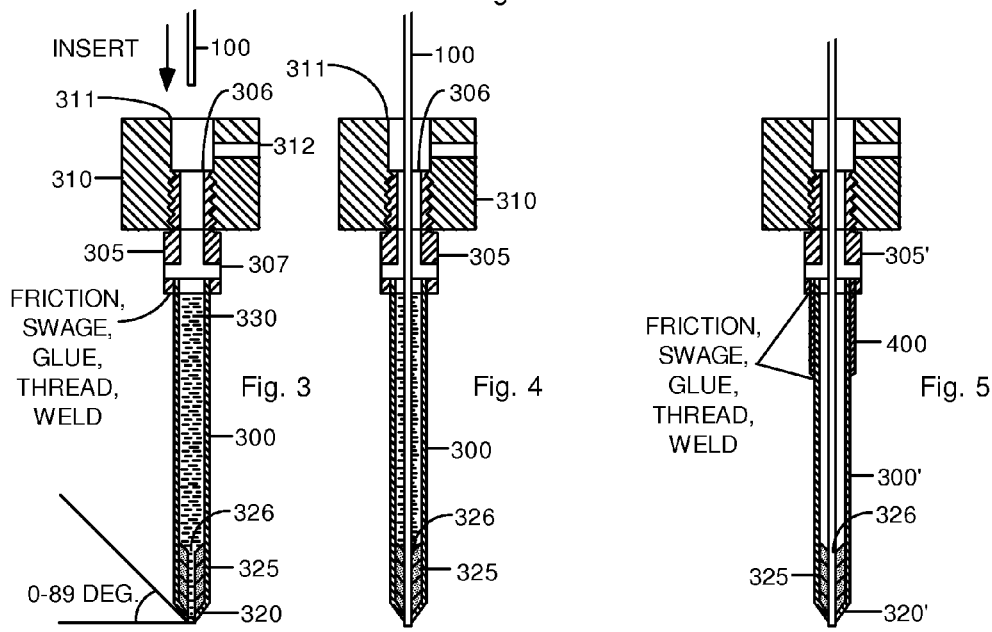

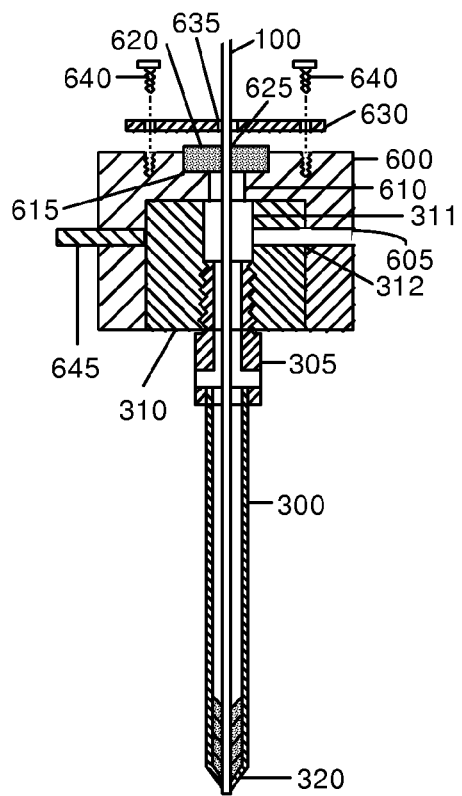
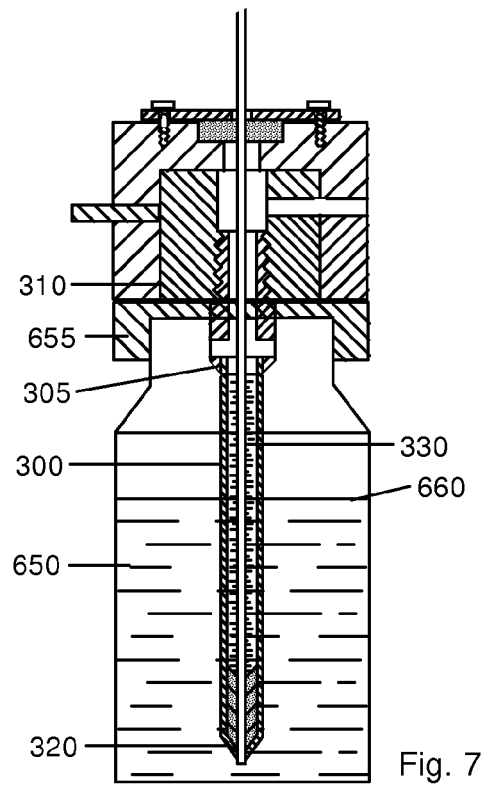
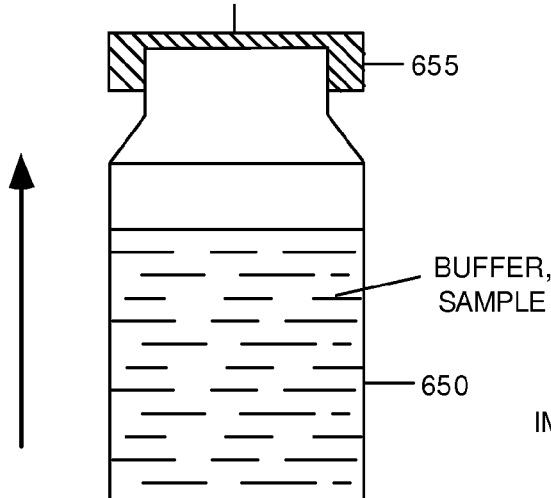
Fig. 6
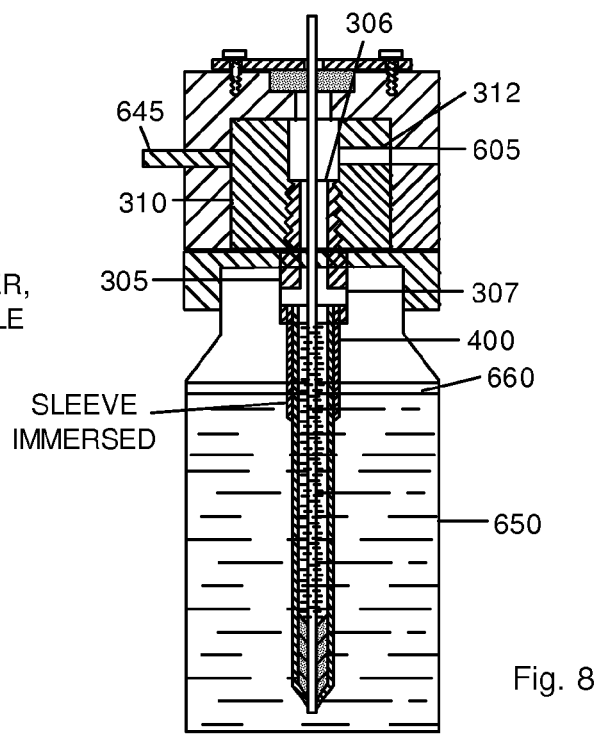
Fig. 8

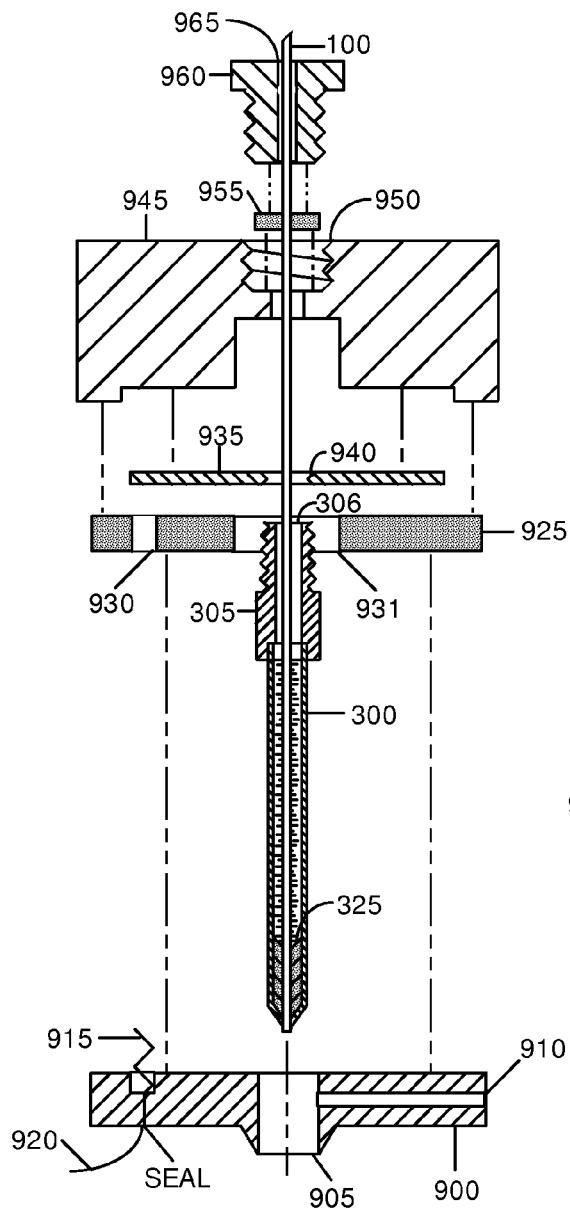
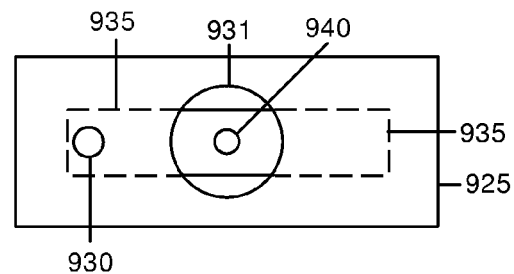
Fig. 10
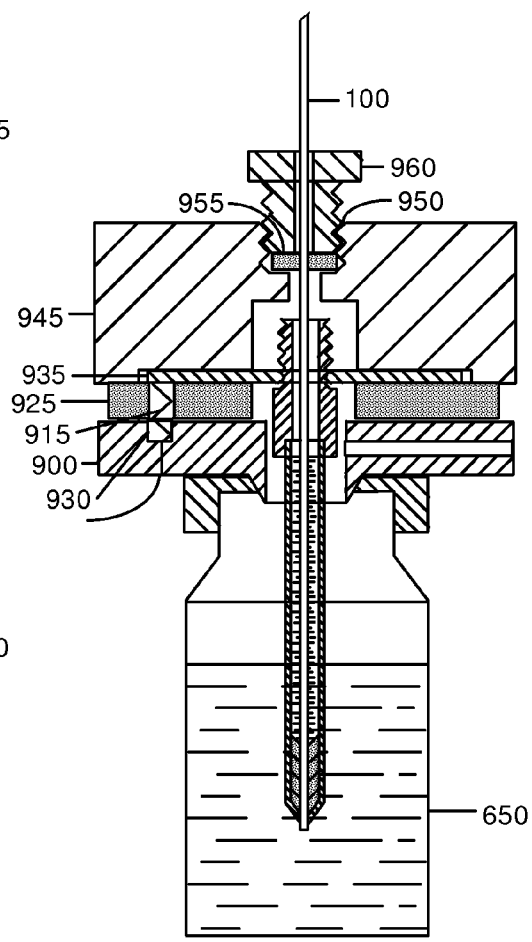
Fig. 9
Fig. 11

ELECTRODE FOR CAPILLARY ELECTROPHORESIS

BACKGROUND

Prior Art—Electrophoresis—FIGS. 1-4

Electrophoresis is a powerful and well-known method that is used in many fields of science to separate molecules having different sizes and different intrinsic electrical charges in order to analyze and synthesize chemical compounds. It is used in DNA sequencing, in the separation of mixtures of proteins, and the like. Two principal methods for performing electrophoretic separations are in routine use today, the planar gel matrix and capillary electrophoresis. These will now be discussed.

Planar Gel Matrix:

In this method a planar gel matrix (flat body of a gel), such as agarose (a complex carbohydrate polysaccharide obtained from agar), is provided and electrodes are located at opposite edges of the gel. A mixture of ionized, i.e., charged, molecules of a substance to be analyzed is applied or positioned in the gel near a first electrode at one edge of the gel, and an DC electrical potential is applied to the electrodes. Because of their intrinsic electrical charge the electrical potential across the gel urges the ionized molecules to move away from the first electrode and toward the second. The motion of the charged molecules is impeded by the structure of the molecules within the gel. The speed at which the charged molecules move depends upon their size, i.e., smaller molecules having a particular electrical charge move faster through the gel than larger ones with the same charge. Thus the difference in speeds results in separation of the previously mixed molecules. In most cases the various molecular species are not normally visible to the human eye. Prior to separation they are combined with dye molecules or tagged with radioactive atoms in well-known fashion, thus rendering them visible, either by direct visual inspection or through the exposure of the separation to a photographic film. This separation is analyzed to quantify the size and numbers of molecules contained in the original mixture.

Capillary Electrophoresis:

The second method, capillary electrophoresis (CE), is used by analytical chemists to separate, in a substance, ionic species from mixtures of chemical compounds. Instead of the planar-gel arrangement described above, CE employs a narrow tube (capillary) through which the molecules move. The different molecules in the substance separate while moving due to the fact that different molecules have different movement speeds within the capillary.

The present patent relates to the second method, CE. FIGS. 1 and 2 are schematic drawings of a prior-art apparatus for performing a CE separation using an "on-capillary" detection. "On-capillary" means the point at which the separation is detected is in a section of the tube or capillary that is used in the actual separation, i.e., there is no separate detection cell. The apparatus comprises a capillary tube 100, a source of DC electrical potential 105, an anode 110, and a cathode 115. Cathode 115 and anode 110 are respectively connected to source 105 by electrical conductors 135 and 130. A light source 120 and a detector 125 arranged so shine light through tube 100. Tube 100 is filled with a matrix substance such as a buffer solution 140, i.e., one that resists changes in pH when small quantities of a base or acid are added to it. The ends of capillary tube 100 are inserted into solutions contained in vials or other containers 116, 117, and 118. Capillary tube 100 is typically made of glass or quartz and has a narrow bore (internal diameter) ranging between 50 and 100 microns (2 to 4 mils), an outer diameter of 200-360 microns (8 to 14 mils), and length of 20 to 50 cm (8 to 20 in.), although other sizes are used.

FIG. 1 shows the apparatus being loaded with a sample mixture 145 of an ionic species, such as biological molecules, having an intrinsic electrical charge. In this case, the intrinsic electrical charge of the molecules is positive so that they will move away from anode 110 toward cathode 115 as they are separated. If the intrinsic molecular charge is known to be negative, the electrical source polarity would be reversed, or the sample can be introduced at the cathode. The right-hand end of capillary 100 and cathode 115 are immersed in a buffer solution 140 in vial 118.

To load sample 145, electrical source 105 and light source 120 are de-energized. Vial 116 containing a solution of sample 145 to be separated is positioned so that anode 110 and the left-hand end of capillary 100 are immersed in sample solution 145. A small amount of the sample is urged into capillary 100, using either hydrostatic pressure or a brief application of electrical potential from source 105, in well-known fashion. After introduction of the sample, vial 116 is removed and replaced with vial 117 (FIG. 2) so that, prior to separation, the sample forms a band in a uniform matrix.

FIG. 2 shows the prior-art apparatus of FIG. 1 in use. Electrical source 105 and light source 120 are energized. Detector 125, such as a photodiode or photomultiplier tube, is connected to a computer 200 or other data recorder. An DC electric field is established between anode 110 and cathode 115 within matrix 140 in capillary tube 100. This field urges the molecular components comprising sample 145 (FIG. 1) to move toward the cathode. As explained, the smaller molecules move faster within matrix 140 and are thus separated from the slower-moving larger molecules. Light source 120 and detector 125 are located near cathode 115 since separation of the molecular species will be greatest at that location. Light source 120 emits a predetermined wavelength or band or bands of wavelengths of light of known intensity. Light from source 120 is arranged to shine through matrix 140 in capillary tube 100 and then onto detector 125. When illuminated, the molecules in sample 145 either absorb or absorb and re-emit light that is captured by detector 125. The intensities of the incident light from source 120 and the light reaching detector 125 are compared and recorded in computer 200 for later analysis. Sample concentration is calculated using a well-known formula, the Beer-Lambert law, explained, e.g., at http://en.wikipedia.org/wiki/Beer%E2%80%93Lambert_law, q.v.

Electrodes 110 and 115 are shown schematically in FIGS. 1 and 2. I have found that prior-art electrode designs did not perform optimally since contamination of the sample and overheating at the electrodes occurred.

The following is a list of some possibly relevant prior art that shows prior art CE electrodes. Following this list I provide a discussion of these references.

| U. S. patents | | | |
|---|---|---|---|
| patent or Pub. Nr. | Kind Code | Issue or Pub. Date | Patentee or Applicant |
| 5,037,523 | B1 | Aug. 6, 1991 | Weinberger et al. |
| 5,364,521 | B1 | Nov. 15, 1994 | Zimmermann |
| 7,662,269 | B2 | Feb. 16, 2010 | Maeshima et al. |

NON-PATENT LITERATURE

Musheev et al., Analytical Chemistry, Vol. 82, 2010, pp 8692-95

Weinberger shows a temperature controlled, air-cooled cartridge for CE. The ends of a capillary tube each pass through the center of an electrode that has an inside diameter slightly larger than that of the outside diameter of the capillary. They extend a short distance beyond the ends of their respective electrodes before entering a manifold. Although Weinberger discusses applying pressure and vacuum for the purposes of filling and flushing the capillary tube, he does not show details of how the electrode tube is sealed in order to accomplish this.

Zimmermann shows a CE apparatus comprising a pair of housings, each with a sealing and electrode arrangement, and a removable cassette that contains a capillary tube. The ends of the capillary tube extend outside the cassette at predetermined locations. Each housing contains a funnel, a silicone rubber seal with a central bore beneath the funnel, and a tubular electrode beneath the seal. The axes of the funnel, the bore of the seal, and the electrode are aligned so that a capillary tube can be inserted through all three parts, with the end of the capillary tube extending beyond the end of the electrode. The funnel is movable over a short distance within the housing. When a cassette is inserted into the CE apparatus the capillary tube is passed through the funnel and out beyond the end of the electrode a predetermined distance where it can be inserted into various solutions as desired. In use, the lower end of the cassette is urged against the upper end of the funnel pressing the lower end of the funnel downward against the seal, thereby compressing it. When the seal is compressed, it prevents passage of fluid or gas (either from pressure or vacuum) through the housing. Samples and solutions can then be urged into or out of the capillary by applying differential pressure or vacuum to the two ends of the capillary tube. There is a slight gap between the outside of the capillary tube and the inside of the electrode tube. This is necessary to permit slidable insertion of the capillary tube into the electrode tube. In this case, unwanted materials such as previously analyzed samples can lodge in the space between the capillary and electrode tubings and cause cross-contamination of samples.

Maeshima shows a simple arrangement for holding the ends of a capillary tube. In a first embodiment, the end of at least one capillary is secured in an insulating member adjacent a wire electrode. Capillary tubing is very fragile and easily damaged when unintended force is applied. This embodiment exposes the ends of the very fragile capillary to damage and, although inexpensive and simple, is vulnerable to breakage. In a second embodiment, the end of at least one capillary is passed through an electrode tube and the electrode tube is secured to the insulating member. As in Zimmerman, there is a slight gap between the outside of the capillary tube and the inside of the electrode tube. This is necessary to permit slidable insertion of the capillary tube into the electrode tube. In this case, unwanted materials such as previously analyzed samples can lodge in the space between the capillary and electrode tubings and cause cross-contamination of samples.

Musheev et al. discuss Joule heating as it affects CE. The migration of species within a CE capillary tube is caused by an electrical potential that is applied between the ends of the capillary. A current flows because of the applied potential. The power associated with the applied potential and resultant current results in Joule (i.e. electrical) heating of the CE capillary tube. Excess heating is known to adversely affect the quality of separation and detection in CE analyses. Although they take Joule heating into account elsewhere along the capillary tube, none of the above patent references minimize Joule heating in the vicinity of the CE electrodes.

Many liquid samples for CE analysis are stored in sealed vials that have a septum at the top. Rather than remove a cap or lid from the vial to reach the sample, a piercing means is urged through the septum and into the sample.

I have found that Joule heating in the vicinity of the electrodes, cross-contamination, and piercing septum are three significant issues in electrode design. None of the prior-art references addressed all three issues. Maeshima's first embodiment is good for heat dissipation but cannot pierce a septum. Weinberger's and Zimmermann's designs can pierce a septum but have poor heat dissipation and are subject to cross-contamination. Thus the above-described references are each useful for their intended purposes but each has one or more disadvantages as noted.

SUMMARY

I have discovered a new design that overcomes some limitations of the prior art. In one aspect, my design comprises a capillary tube, a sheath that is rigidly joined to a connector, and a seal between the inner wall of the sheath and the outer wall of the capillary. My design is strong enough to penetrate the septum of a sample vial, reduces or eliminates cross-contamination of samples, and provides for cooling the capillary tube in the vicinity of the electrode.

DRAWING FIGURES

Figure 13:
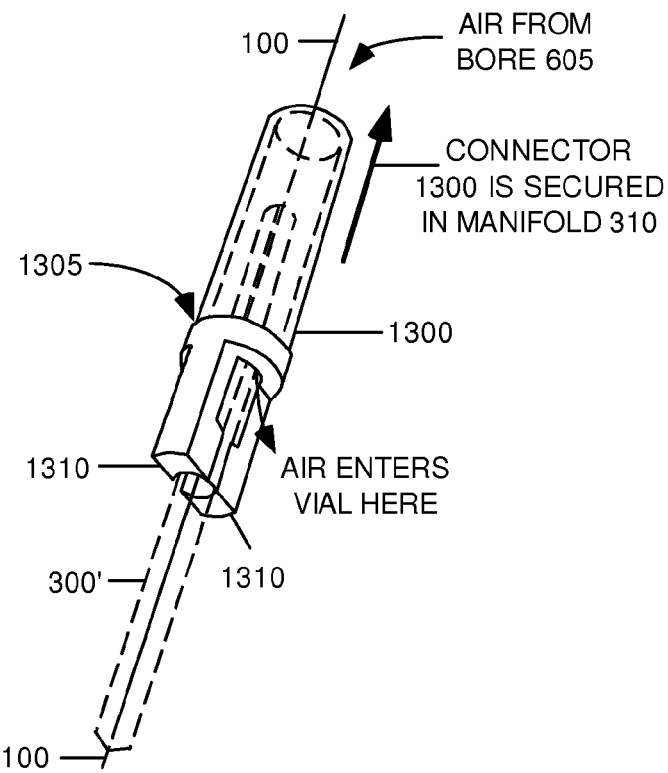

FIGS. 1 and 2 show a prior-art CE system.
FIGS. 3 and 4 show aspects of a first embodiment.
FIG. 5 shows one aspect of an alternative embodiment.
FIGS. 6 and 7 show the embodiment of FIGS. 3 and 4 in use.
FIG. 8 shows the embodiment of FIG. 5 in use.
FIGS. 9 through 11 show aspects of a third embodiment.
FIGS. 12 and 13 show alternative aspects of the embodiment of FIGS. 3 and 4.

| DRAWING REFERENCE NUMERALS | | | |
|---|---|---|---|
| 100 | Capillary tube | 105 | Electrical source |
| 110 | Anode | 115 | Cathode |
| 116 | Container | 117 | Container |
| 118 | Container | 120 | Light source |
| 125 | Detector | 130 | Conductor |
| 135 | Conductor | 140 | Matrix |
| 145 | Sample | 200 | Computer |
| 300 | Sheath | 305 | Connector |
| 306 | Bore | 307 | Bore |
| 310 | Manifold | 311 | Bore |
| 312 | Bore | 320 | Piercing point |
| 325 | Seal | 326 | Lumen |
| 330 | Liquid | 400 | Sleeve |
| 600 | Housing | 605 | Bore |
| 610 | Bore | 615 | Bore |
| 620 | Seal | 625 | Lumen |
| 630 | Plate | 635 | Hole |
| 640 | Fastener | 645 | Electric contact bar |
| 650 | Vial | 655 | Cap |
| 660 | Solution | 900 | Seat fitting |
| 905 | Bore | 910 | Bore |
| 915 | Spring | 920 | Conductor |
| 925 | Seal | 930 | Opening |
| 931 | Opening | 935 | Plate |
| 940 | Opening | 945 | Cartridge housing |
| 950 | Aperture | 955 | Seal |
| 960 | Nut | 965 | Bore |

-continued

| DRAWING REFERENCE NUMERALS | | | |
|---|---|---|---|
| 1200 | Connector | 1205 | Bore |
| 1210 | Bore | 1300 | Connector |
| 1305 | Shoulder | 1310 | Fingers |

DESCRIPTION

First Embodiment—FIGS. 3 Through 5

FIGS. 3 through 5 show sectional side views of two aspects of a first embodiment.

In the prior-art apparatus of FIGS. 1 and 2, the end of capillary tube 100 is merely positioned below the surface of the contents of containers 116, 117, and 118. In many cases, such containers are sealed at the top by a thin membrane, usually rubber, as described below. The membrane must be pierced so that capillary tube 100 can be inserted into these contents. Capillary tube 100 doesn't have sufficient strength to pierce a membrane by itself and a strengthening element is required. When the prior-art apparatus is in use, Joule heating at the electrodes can cause decomposition of the sample being separated.

First Aspect.

FIGS. 3 and 4 show a first aspect of a first embodiment of a capillary electrophoresis electrode. Instead of an isolated metal wire electrodes 110 and 115 in FIGS. 1 and 2, a tubular electrode is designed to provide both thermal and mechanical protection for the end of capillary tube 100.

In this aspect, a tubular metal sheath 300 (FIG. 3) is rigidly joined to an electrically conductive connector 305. The joint between sheath 300 and connector 305 is formed by a friction fit, swaging, gluing, welding, or threading. Connector 305 is secured in a manifold 310 by threading, although a friction fit or swaging, gluing, or welding can be used. The lower end of sheath 300 is beveled to form a piercing point 320 that is used to pierce a rubber membrane, as described below. The angle formed by piercing point 320 with respect to the axis of sheath 300 can be selected from 0 to nearly 90 degrees as shown in FIG. 3. The angle is determined by the thickness and hardness of the membrane to be pierced, the expected ease of piercing, and the strength and stiffness of sheath 300 so that sheath 300 is not bent as it enters the membrane. In some cases, there will be no requirement for piercing a membrane so piercing point 320 can have any angular shape.

Connector 305 has a central axial bore 306 and a radial bore 307. Manifold 310 has a central axial bore 311 that is contiguous with bore 306 of connector 305, and also a radial bore 312. Bores 306, 307, 311, and 312 form an air path for a purpose described below.

FIG. 3 shows a capillary tube 100 in position above manifold 310 in preparation for installation into sheath 300. The lower end of sheath 300 contains an inner elastomeric seal 325. Seal 325 has an inner lumen 326 with diameter slightly less than the outer diameter of capillary tube 100. Seal 325 is a pliable elastomer such as silicone rubber, although other materials can be used.

FIG. 4 shows capillary tube 100 fully installed into sheath 300. Capillary tube 100 is inserted into sheath 300 by passing it through bore 311 of manifold 310, bore 306 of connector 305, and lumen 326 of seal 325. Capillary 100 extends a short distance, on the order of 0.5 to 1.0 mm, beyond the lower end of sheath 300.

FIGS. 3 and 4 show a liquid 330 contained within sheath 300. In a first option, capillary tube 100 is installed and then water 330 is added to sheath 300 via bores 311 and 306 or bore 307 and fills sheath 300 to a point about 1 mm below bore 307. Alternatively, sheath 300 can be immersed in a vial of liquid to a depth about 1 mm below bore 307 and liquid 330 flows into sheath 300 via lumen 326 of seal 325. Capillary tube 100 is then installed, sealing the liquid within sheath 300. Liquid 330 cools capillary 100 within sheath 300. Liquid 330 is water, although other fluids, such as ethylene glycol, or a mixture of water and ethylene glycol can be used.

Second Aspect.

FIG. 5 shows a second aspect of the first embodiment. A tubular plastic sheath 300' is used instead of metal sheath 300 (FIG. 3). Sheath 300' is secured and sealed within a metal sleeve 400 that in turn is rigidly joined to a metal connector 305'. Both are secured by a friction fit, swaging, gluing, threading, or welding. As in the first aspect, a capillary 100 extends downward through an electrically conductive connector 305' and sheath 300', exiting and extending a predetermined distance below the bottom of sheath 300'. As it exits sheath 300', capillary 100 passes through a lumen 326 in a rubber seal 325 that blocks the passage of liquids and gasses past the bottom of capillary 100. As before, the bottom of sheath 300' optionally includes a beveled region 320' which may or may not have the same angle with respect to sheath 300' as piercing point 320 has to sheath 300 (FIG. 3).

Sheaths 300 and 300' are typically 20-30 mm long, with inner diameter of 0.8-1.0 mm and outer diameter of 1.2-1.6 mm. Sheath 300 is made of stainless steel, aluminum, platinum, or a metal alloy. Sheath 300' is made of polypropylene, PEEK (PolyEtherEtherKetone), or any other suitable plastic that does not bend or break when used and which is chemically inert with respect to the CE being performed. Seal 325 is about 3 mm long. Piercing points 320 and 320' are typically angled at 30 degrees with respect to the axis of sheaths 300 and 300'. Other dimensions can be used.

OPERATION

First Embodiment—FIGS. 6 to 8

FIG. 6 shows an exploded cross-sectional view of one aspect of the present embodiment in preparation for use. Capillary 100 is installed in sheath 300 which in turn is installed in connector 305 and connector 305 is installed in manifold 310. Manifold 310 is installed in a housing 600. Housing 600 is normally rigidly mounted in a CE apparatus (not shown). Housing 600 is electrically insulative in this aspect, although it can be electrically conductive provided it is mounted safely in order to prevent electrical shocks and shorts.

Housing 600 includes a first bore 605 that communicates with bore 312 in manifold 310, allowing the passage of air, and a second bore 610 that communicates with bore 311 in manifold 310, allowing the passage of capillary 100. Housing 600 also includes a third bore 615 contiguous with second bore 610. An elastomeric seal 620 is installed in bore 615. Seal 620 has a central lumen 625 through which capillary 100 is passed as capillary 100 is prepared for installation in the overall CE apparatus (not shown). A pressure plate 630 is installed above seal 620. Plate 630 has a central hole 635, slightly larger in diameter than capillary tube 100, for the passage of capillary tube 100 into the remainder of the CE apparatus. A pair of fasteners 640 are used to secure plate 630 to housing 600. When fasteners 640 are tightened, plate 630 compresses seal 615 around capillary tube 100, securing it in place in housing 600.

An electric contact bar 645 passes through a wall of housing 600 and makes firm mechanical and electrical contact with manifold 310. Thus electric contact bar 645 is electrically connected to electrode 300 via manifold 310 and connector 305. Electric contact bar 645 is connected to a CE power source during the CE process. It is made of a suitable metal such as copper, stainless steel, aluminum, or an alloy and is of sufficient diameter to pass the current required for CE with negligible voltage drop along its length.

A vial 650 containing either a sample or buffer solution 660 is shown at the bottom of FIG. 6. Vial 650 is sealed with a well-known puncturable membrane cap 655. When the CE apparatus is in use, vial 650 is urged upward, as indicated by the vertical arrow. The pointed bottom 320 of sheath 300 pierces cap 655 and in inserted into vial 650 until the top of cap 655 rests firmly against the bottom of manifold 310.

FIG. 7 shows the apparatus of FIG. 6 ready for use. The full length of electrode 300 is within vial 650 and piercing point 320 is immersed in the fluid contained in vial 650. In addition, the lower end of connector 305 has also punctured cap 655 so that bore 307 lies entirely beneath cap 655. The bottom circumference of connector 305 is beveled to further facilitate the penetration of connector 305 through cap 655. Fasteners 640 are tightened, urging plate 630 against the top of housing 600 and compressing seal 625 against capillary tube 100 and sealing against air leakage via the top of housing 600.

FIG. 8 shows the assembly of FIG. 5 installed and ready for use. In this case, fluid 660 in vial 650 must be in contact with metal sleeve electrode 400. The depth of sleeve 400 in fluid 660 depends on the requirements for a specific CE application.

During CE analysis, bore 605 is connected to a pressurized air (or other gas) source (not shown). Air is urged into vial 650 through bores 605, 312, 306 and 307 and the local increase in pressure urges fluid 660 to enter capillary tube 100 in order to load a quantity of sample or buffer solution into capillary tube 100 for separation. The details of loading capillary tube 100 are discussed above. Electric current passes from a power supply (not shown) through contact bar 645, manifold 310, connector 305, sleeve 400, and solution 660 to enter matrix 140 (FIG. 1). IT then passes through matrix 140 to the distal end of capillary tube 100, another electrode at the distal end of capillary tube 100, and finally returns to the power supply.

In both aspects of the present embodiment, water 330 (or other fluid) within sheath 300 has sufficient heat capacity to absorb heat and cool capillary tube 100 during a CE separation. In addition, water 330 has sufficient thermal conductivity to conduct heat from capillary tube 100 to sheath 300 and then on to fluid 660 in order to provide additional cooling. Therefore, my new electrode alleviates Joule heating in the vicinity of the CE electrodes.

DESCRIPTION AND OPERATION

Alternative Aspects—FIGS. 9 to 13

Prior art CE apparatuses frequently provide a CE capillary tube and various associated fittings in cartridge form so that an operator can easily change capillary tubes. FIGS. 9 through 11 show the above embodiments incorporated into a cartridge format.

FIG. 9 is an exploded view of the present aspect showing an easily assembled and disassembled cartridge unit. An electrode assembly according to the first aspect described above is used as an example here, but the second aspect described above can also be used interchangeably.

The first structure is a seat fitting 900 which is fixed on instrument frame (not shown) and contains a first bore 905. A second bore 910 provides an air conduit between bores 905 and outside source. An electrically conductive spring 915 extends upward from seat fitting 900. An electrical conductor 920 is connected to spring 915 and is sealed where it passes through seat fitting 900. Conductor 920 is connected to the CE power supply (not shown) during use.

Above seat fitting 900 is a removable elastomeric seal 925. An opening 930 at left side of seal 925 is positioned above spring 915 and has diameter sufficient to allow spring 915 to freely pass therethrough. An opening 931 in middle of seal 925 has diameter sufficient to allow connector 305 and air to pass therethrough.

An electrically conductive plate 935 is shown above seal 925. Plate 935 has a threaded aperture 940 with threads that match those on connector 305. During assembly, connector 305 is threadably secured into plate 935.

A cartridge housing 945 is shown above plate 935. In preparation for use, plate 935 is affixed to housing 945 using fasteners, glue, etc. in order to simplify assembly of the various components shown in FIGS. 9-11. Seal 925 may also be fixed temporarily to housing 945 to facilitate assembly.

FIG. 10 is a bottom view of seal 925 and plate 935 showing their relative positions and sizes.

Housing 945 also includes a threaded aperture 950. An elastomeric seal 955 is positioned above aperture 950 and sized to easily fit into aperture 950. A threaded nut 960 is positioned above housing 945. A central bore 965 in nut 960 is sized to pass a capillary 100 in preparation for use.

Sheath 300 with internal seal 325 is secured to connector 305 that has bore 306, but bore 307 is omitted, as shown. Air can move up through bores 905, 931 and 306 to reach the content of sheath 300 and move down through bore 905 to vial 650. Since the first aspect described above is used in this example, sheath 300 is electrically conductive and is secured and electrically connected to connector 305.

FIG. 11 shows a cross-sectional view of the apparatus of FIG. 9 assembled and ready for use. Capillary 100 has been inserted as described above. Nut 960 has been threadably secured within aperture 950 of cartridge housing 945, compressing seal 955 around capillary 100, thereby providing a pressure seal and mechanical clamping action to hold capillary 100 in place. Seat fitting 900 is fixed on a CE apparatus (not shown) by a clamp, screws, or other means (not shown). By urging cartridge housing 945 from the top and vial 650 from the bottom against the apparatus, an air-tight chamber is formed. At same time, spring 915 has passed through opening 930 in seal 925 and is in secure electrical contact with plate 935.

FIG. 12 shows a cross-sectional view of another alternative aspect of the apparatus of FIG. 7. Capillary 100 is secured within a metal sheath 300', as described above in connection with FIG. 7. Connector 305 is replaced by a modified connector 1200 which has a wider bore 1205 that allows sheath 300' to pass through it. Sheath 300' is secured within a hole 1202 at the bottom of connector 1200 by friction, swaging, gluing, threading, soldering, welding, or the like. Connector 1200 is secured within manifold 310 by one or more of the same means, i.e. friction, etc. Connector 1200 includes two bores: an axial bore 1205 and a radial bore 1210. Air flow from the entrance of bore 605 to the inside of vial 650 is now communicated through bores 1205 and 1210. This aspect of the embodiment provides a longer cooling bath than that described above.

FIG. 13 shows a perspective view of an alternative connector for creating an air passage and holding sheath 300'. Connector 1300 is an electrically conductive holder for a sheath 300' into which a capillary 100 is inserted, as described above. Connector 1300 has a central bore that is larger in diameter than sheath 300'. Sheath 300' is inserted into connector 1300 from either end and is secured by a pair of fingers 1310 by gluing, threading, soldering, welding, or the like. Sheath 300' projects a predetermined distance below connector 1300. Connector 1300 further includes a shoulder 1305. In use, connector 1300 is secured within manifold 310, by threading or other means described above. Air from bore 605 in manifold 310 (FIG. 12) passes into connector 1300 at its top end and exits below shoulder 1305, as shown by the lower arrow in FIG. 13. Connector 1300 has larger opening and straight passage for airflow than connector 305 and 1200.

Compared to the previous designs, the cartridge embodiment (FIGS. 9-11) makes changing capillary tubes easier and provides a longer cooling section for the capillary tube. Both alternative connectors 1200 (FIG. 12) and 1300 have longer cooling section.

CONCLUSIONS, RAMIFICATIONS, AND SCOPE

I have provided an improved electrode assembly for use in CE. In the past, Joule heating concentrated at the electrode and could degrade samples locally and cause errors in CE analyses. I have alleviated this Joule heating by placing a thermally conductive water bath around the end of the capillary tube that is near or inside the electrode. Therefore CE analyses performed using my electrode assembly do not present as much uncertainty as with heating at that point. In addition, my electrode also reduces cross-contamination by the electrode while it has sufficient mechanical strength to pierce a septum.

While the above description contains many specificities, these should not be construed as limitations on the scope, but as exemplifications of some present embodiments. Many other ramifications and variations are possible within the teachings herein. For example, metal electrode 300 in FIG. 3 can be divided into two sections: a beveled tip section and a simple tubing section. These two sections can be manufactured separately and then welded or otherwise bonded together. Similarly, sleeve 400 in FIG. 5 can be long and the plastic tubing 300' can be very short, making it a metal electrode with plastic beveled tip. In some cases, the beveled tip can be eliminated. Sleeve 400 and connector 305' in FIG. 5 can be machined as one piece. Sleeve 400 can be replaced by a metal coating or plating. Bore 307 on connector 305 can be eliminated and water can be filled up to bore 312, while air pressure or vacuum will be applied through an additional channel or from the other end of the capillary. A plastic sheet or cap can be attached to the lower surface of manifold 310 in order to improve chemical resistance.

Thus the scope should be determined by the appended claims and their legal equivalents, rather than the examples and particulars given.

The invention claimed is:

1. An electrode for use in capillary electrophoresis, comprising:
    an electrically conductive connector with a bore,
    a tubular sheath having an axis, a bore, and first and second ends,
    said tubular sheath being secured to said connector at a location selected from said first end and between said first and said second ends,
    a capillary tube,
    an elastomeric seal located within said bore of said sheath at said second end, said seal having a bore of diameter equal to or less than the outer diameter of said capillary tube so as to permit said capillary tube having a predetermined diameter to sealably pass therethrough,
    a liquid inside said sheath and above said elastomeric seal so that when said capillary tube is passed through said bores of said tubular sheath and said seal, said sheath contains said liquid, and
    whereby when said electrode is energized and heat from Joule heating occurs within said capillary tube, said liquid absorbs and conducts heat from said capillary tube to said tubular sheath and said tubular sheath dissipates said heat into the ambient surrounding said sheath region, thereby cooling said capillary tube by conducting said heat away from said capillary tube and into said region.

2. The electrode of claim 1 wherein said second end of said sheath is beveled at a predetermined angle selected between 0 and 89 degrees relative to said axis of said sheath.

3. The electrode of claim 1 wherein said sheath is made of materials selected from the group consisting of metal and plastic.

4. The electrode of claim 3 wherein said plastic includes plastics selected from the group consisting of polypropylene and polyetheretherketone.

5. The electrode of claim 3 wherein when said tubular sheath is made of plastic, said electrode further includes a tubular and electrically conductive sheath surrounding said plastic sheath and connected to said connector at said first end of said sheath and extending a predetermined distance away from said first end of said sheath toward said second end of said sheath.

6. An electrode assembly for use in capillary electrophoresis, comprising:
    a housing,
    an electrically conductive manifold secured within said housing,
    an electrically conductive bar connected to said manifold and extending a predetermined distance outside said housing for connecting said electrode to an electrical potential source,
    a electrically conductive connector secured to said manifold,
    a sheath, said sheath fillable with liquid and having first and second ends, said first end being secured to said connector, said second end of said sheath being pointed for puncturing a puncturable seal on a vial that contains a fluid,
    a elastomeric seal secured within said sheath at said second end, said seal having a bore of diameter equal to or less than the outer diameter of a capillary tube of a predetermined size so as to permit such a capillary tube to sealably pass therethrough,
    said housing, said manifold, said connector, said sheath, and said seal each containing a first bore, said first bores of said manifold, said connector, said sheath being collinear,
    said housing, said manifold, and said connector each further including a second bore, said second bore of said manifold, said connector, said sheath being contiguous and providing a path for gas from outside said housing through said connector,
    whereby when a capillary tube is passed through all of said first bores starting at said bore in said manifold and extending a predetermined distance beyond said end of said sheath, and said sheath is filled to a predetermined depth with liquid, and said vial is urged against said sheath so that said sheath punctures said seal on said vial and said vial is further urged against said manifold so that said connector also punctures said seal on said vial so that said sheath and said bore of said connector lie within said vial, an air path will be provided from within said vial to outside said housing, so that a cooled electrode with an air passage for capillary electrophoresis is provided.

7. The electrode assembly of claim 6 wherein said sheath is made of materials selected from the group consisting of metal and plastic.

8. The electrode assembly of claim 7 wherein said plastic includes plastics selected from the group consisting of polypropylene and polyetheretherketone.

9. The electrode of claim 7 wherein when said tubular sheath is made of plastic, said electrode further includes a tubular and electrically conductive sheath surrounding said plastic sheath and connected to said connector at said first end of said sheath and extending a predetermined distance away from said first end of said sheath toward said second end of said sheath.

10. The electrode assembly of claim 6 wherein air pressure within said second bore in said housing is equal to air pressure within said vial.

11. The electrode assembly of claim 6 wherein said liquid is selected from the group consisting of water, ethylene glycol, and a mixture of water and ethylene glycol.

12. The electrode assembly of claim 6, further including a third bore in said housing that is coaxial with said first bore and having a diameter greater than said first bore, a cylindrical elastomeric seal slidably seated within said third bore and having a central hole, said seal extending a predetermined distance outside said housing, a pressure plate with a central hole, and at least one fastener, whereby when said capillary is passed through said hole in said plate and said hole in said seal and said pressure plate is urged against said housing, said seal is compressed and provides a pressure seal between said capillary and said housing.

13. An electrode cartridge assembly for use in capillary electrophoresis, comprising:
  a housing with upper and lower surfaces, said housing including a threaded bore with internal threads at said upper surface,
  a compressible elastomeric upper seal insertable into said threaded upper bore of said housing and having a central bore having sufficient diameter to allow a capillary tube having a predetermined size to slidably pass therethrough when said seal is not compressed and to form an airtight seal against said capillary tube when said seal is compressed,
  a nut having external threads and a central bore with sufficient diameter to allow said capillary tube to slidably pass therethrough wherein said nut threadably mates with said threaded upper bore of said housing for compressing said elastomeric upper seal against said capillary tube when said nut is threadably secured, and
  an electrically conductive plate located beneath said lower surface of said housing, said plate further including a central threaded opening,
  a connector with first and second ends, said first end of said connector being externally threaded and secured to said electrically conductive plate, and said second end of said connector having a bore of predetermined diameter,
  a tubular sheath having a bore and first and second ends, said tubular sheath being secured to said connector at said first end of said sheath by being securably inserted into said bore at said second end of said connector, and said second end of said sheath having a pointed end,
  a first elastomeric seal located within said bore of said sheath at said second end, said first elastomeric seal having a bore of diameter equal to or less than the outer diameter of a capillary tube so as to permit a capillary tube to sealably pass therethrough,
  a seat fitting with a centrally located axial bore having sufficient diameter to allow said connector to freely pass therethrough, said seat fitting further including a spring contact with first and second ends, said first end of said spring contact extending above an upper surface of said seat fitting and arranged to springably contact said electrically conductive plate, and said second end of said spring contact extending out and away from said seat fitting, said seat fitting further including a radial bore therethrough in communication with said axial bore,
  a second elastomeric seal located between said housing and said seat fitting and arranged to urge said electrically conductive plate against said housing when said second elastomeric seal is urged by said seat fitting, said seal further including first and second bores, said first bore being centrally located and of sufficient diameter to freely pass said connector, and said second bore being located adjacent said spring and having sufficient diameter to permit said spring to pass therethrough,
  whereby when said seat fitting, said second elastomeric seal, and said housing are urged together, said spring contact makes electrical contact with said electrically conductive plate and said electrically conductive tubular sheath extends through said centrally located axial bore of said seat fitting, whereupon said electrode cartridge assembly is ready for use.

14. The electrode assembly of claim 13 wherein said tubular sheath is made of materials selected from the group consisting of metal and plastic.

15. The electrode assembly of claim 14 wherein said plastic is selected from the group consisting of polypropylene and polyetheretherketone.

16. The electrode of claim 14 wherein when said tubular sheath is made of plastic, said electrode further includes a tubular and electrically conductive sheath surrounding said plastic sheath and connected to said connector at said first end of said sheath and extending a predetermined distance away from said first end of said sheath toward said second end of said sheath.

17. The electrode assembly of claim 13 wherein said electrically conductive plate is affixed to said lower surface of said housing.

\* \* \* \* \*